United States Patent
Holtund et al.

(12)

(10) Patent No.: US 6,225,072 B1
(45) Date of Patent: May 1, 2001

(54) PROCESS FOR THE EXTRACTION OF PROTEINS

(75) Inventors: Jostein Holtund; Siri Dale; Magne K Fagerhol, all of Oslo (NO)

(73) Assignee: Magne K. Fagerhol, Oslo (NO)

( * ) Notice: Subject to any disclaimer, the term of this patent is extended or adjusted under 35 U.S.C. 154(b) by 0 days.

(21) Appl. No.: 09/303,611

(22) Filed: May 3, 1999

Related U.S. Application Data

(63) Continuation of application No. PCT/GB97/03013, filed on Nov. 3, 1997.
(60) Provisional application No. 60/042,223, filed on Apr. 15, 1997.

(30) Foreign Application Priority Data

Nov. 1, 1996 (GB) .................................................. 9622839
Apr. 8, 1997 (GB) .................................................. 9707148

(51) Int. Cl.⁷ .................................................. G01N 33/53
(52) U.S. Cl. ........................... 435/7.92; 436/66; 436/518; 436/813; 530/412; 530/422
(58) Field of Search ............................... 435/7.92, 12, 25, 435/26, 803, 810; 530/350, 380, 712, 827, 422; 436/66, 518, 813

(56) References Cited

U.S. PATENT DOCUMENTS 4,833,074    5/1989    Fagerhol et al. .
5,139,934 *  8/1992    Stewart et al. ....................... 435/7.92
5,455,160   10/1995    Fagerhol et al. .

FOREIGN PATENT DOCUMENTS 0 281 251 A2    7/1988   (EP) .

OTHER PUBLICATIONS

Satoru Yui, Masaaki Mikami, Kazusa Tsurumaki and Masatoshi Yamazaki, Journal of Leukocyte Biology, Jan. 1997, "Growth–inhibitory and apoptosis–inducing activities of calprotectin derived from inflammatory exudate cells on normal fibroblasts: regulation by metal ions".

Richard A. Finkelstein, Carmen V. Sciortino, and Mark A. McIntosh, Reviews of Infectious Diseases, 5:4, Sep.–Oct. 1983, "Role of Iron in Microbe–Host Interactions".

Mark J. Raftery, Craig A. Harrison, Paul Alewood, Alun Jones and Carolyn L. Geczy, J. Biochem., 1996, "Isolation of the murine S100 protein MRP14 (14 kDa migration–inhibitory–factor–related protein) from activated spleen cells: characterization of post–translational modifications and zinc binding".

Graeme P. Young and D. James B. St. John, Clin, Biochem. Revs., vol. 13, Nov. 1992, "Faecal Occult Blood Tests: Choice, Usage and Clinical Applications".

\* cited by examiner

*Primary Examiner*—Donna Wortman
*Assistant Examiner*—Robert A. Zeman
(74) *Attorney, Agent, or Firm*—Bacon & Thomas

(57) ABSTRACT

The present invention provides a process for the extraction of proteins from gastrointestinal tract samples taken from humans or other mammals wherein the sample is mixed with an excess amount of aqueous extraction medium comprising at least one dissociating, disaggregating and/or chelating agent, homogenised in a closed vessel, the solid and liquid materials of the dispersion are separated from each other and the clear liquid extract is recovered.

25 Claims, No Drawings

PROCESS FOR THE EXTRACTION OF PROTEINS

This application is a continuation of international application number PCT/GB97/03013 filed Nov. 3, 1997 (of which the entire disclosure of the, prior application is hereby incorporated by reference), which itself is a continuation-in-part of U.S. provisional application Ser. No. 60/042,223 filed Apr. 15, 1997.

The present invention relates to a process for extracting proteins from gastrointestinal samples and to new and/or improved methods for the determination of said proteins.

The onset and progression of many diseases results in altered patterns of cellular metabolism, antigenicity and changes in the quantitative and qualitative manufacture of cellular products or secretion or release thereof.

One such type of disease is cancer and of particular interest for the purposes of the present invention is cancer of the gastrointestinal (GI) tract. Cancers more remote from the GI tract and other diseases such as inflammatory and infectious diseases are also included within the scope of the invention.

It has been noted by researchers that certain endogenously produced substances are detected in increased or decreased amounts or in variant forms in samples taken from the GI tract of patients with GI or proximate tissue disease. For example, the protein calprotectin, previously referred to as L1 protein, is released in large amounts from leucocytes into the GI tract in response to some diseases, see e.g. U.S. Pat. No. 4,833,074 and U.S. Pat. No. 5,455,160. Calprotectin, a calcium binding heterocomplex protein comprising two heavy chains and one light chain (Fagerhol, et al., 1990), and as another example the protein haemoglobin, have been found in elevated amounts in the faeces of patients suffering from GI cancer (Roseth et al., (1993); Young & St. John, (1992)).

The detection of abnormal amounts or forms of such indicator proteins could be of great predictive and diagnostic value and may be useful in monitoring the progress of disease and also the efficacy of treatment and/or therapeutic procedures. Moreover, although protein profile changes may be detectable in a sample taken from any section of the GI tract, if the sample is a faecal sample then this could represent an entirely non-invasive method by which diagnostic and prognostic appraisals could be made.

Presently, an operator friendly assay that is sufficiently reliable and accurate is not available to measure the titre of such proteins of gastrointestinal origin. This is principally due to the difficulty in extracting the proteins from GI samples, usually faeces, in a form suitable for direct assay by conventional methods e.g. ELISA.

In U.S. Pat. No. 4,833,074, Fagerhol et al. disclose an antibody based detection system for the calprotectin protein and a method for isolation and purification of calprotectin from granulocytes. Such antibody based methods of quantitative detection work well (as will be discussed in greater detail later) when the protein is extracted from more amenable sources than the GI tract. Obviously however it is highly desirable in many respects that the samples from which proteins of interest should be isolated are faecal in origin.

A further immunoassay based method for determining analytes in faecal samples is disclosed in EP-A-0281251 wherein a sample of stool is dispersed in aqueous solution comprising various preservatives, analyte stabilising agents and endogenous interference reducing agents, the solids are allowed to settle and then the liquid phase used for analyte testing.

In U.S. Pat. No. 5,455,160, Fagerhol et al. disclose a kit and a method for the determination of calprotectin in GI samples. This kit and method are presented as a diagnostic tool for use in the detection of cancer and inflammatory bowel diseases. Clearly, these disclosures represent a useful step in the determination and clinical evaluation of altered protein levels, in samples which originate from the GI tract. This method suffers however from severe disadvantages in respect of quantitative accuracy and reproducibility and the ease with which the procedure may be performed by operators in a laboratory.

Firstly, the method of the above mentioned U.S. Pat. No. 5,455,160 describes the use of a sample size of 5 g of faeces which may prove difficult to obtain from elderly or frail subjects. The necessity for such a large amount of faeces creates some storage problems, especially if the samples require freezing.

More importantly, the method entails the process of homogenising the faeces sample in a comparatively small volume (2×) of buffer, in an open tube using a non-disposable rod mixer. Clearly this introduces some health risk to laboratory personnel on account of the aerosol of faeces formed in the course of the procedure. This may result in environmental and operator contamination, possibly cross-contamination of samples, not to mention containment and cleaning problems and a generally unpleasant environment in which to work. These problems may preclude the routine use of such a method as a clinical tool.

The present inventors have established that the extraction steps of the prior art method normally result in the determination of only some 15 to 30% of the total amount of calprotectin present in the faecal sample (Table 1, Example 4 hereinafter). This finding was arrived at by comparing the amount of calprotectin obtained from a single extraction according to the prior art method with the total amount of calprotectin present in a sample. The total amount of calprotectin in a sample was measured by extracting the same sample five times, so that it was essentially depleted of calprotectin, using a method according to the invention, and then summing the five amounts extracted from the sample.

Furthermore, a considerable amount of variability appears to be inherent in the prior art method.

Furthermore, the end product of the prior art extraction procedure is a suspension comprising a large amount of insoluble, particulate detritus. Such a viscous, particulate supernatant may be unsuitable for use with many quantitative determination methods e.g. those using membrane filters loaded with specific antibodies.

In summary therefore, there is a need for a reliable, practicable method by which proteins of interest may be extracted from samples originating from the GI tract, in particular but not exclusively from faeces, preferably in a form which facilitates their analysis and/or quantitation by any method known to one skilled in the art.

It has now surprisingly been found that by using a much smaller sample than in the prior art, for example 50 to 100 mg of faeces (compared to the 5 g of the prior art), a much more accurate and reproducible quantitative determination of the amount of calprotectin or other endogenous protein can be made. Simultaneously, in the same faecal extract as is used for measurement of calprotectin, one may determine the concentration of other endogenous proteins such as haemoglobin. The present inventors have conceived of a new extraction process which ameliorates the problems of the prior art process and provides a practicable, reliable and operator friendly process for the determination of proteins from GI tract samples.

One aspect of the present invention therefore relates to a process for the extraction of proteins from gastrointestinal (GI) tract samples, including faeces, from humans or other mammals, comprising;
a) mixing a small amount of sample (preferably 10 to 500 mg and more preferably 20–150 mg, optionally pre-weighed) with an excess amount of aqueous extraction medium (preferably in the region of 50 fold excess v/w) comprising at least one dissociating, disaggregating and/or chelating agent as described below,
b) homogenising the sample (preferably by vortexing) in a closed tube,
c) separating the solid and liquid material of the dispersion (preferably by centrifugation and additionally or optionally by filtration), and,
d) recovering the clear liquid extract, also referred to hereinafter as the filtrate or the supernatant;
said extract and proteins therein being susceptible of qualitative and/or quantitative determination using any suitable means.

The smaller sample is easier to collect, store and dilute. Collection of the sample is particularly relevant when considering elderly or frail subjects or when the sample of interest is not faeces but a sample which must be obtained by gastroscopy, endoscopy or any other invasive technique.

The scaling down of the sample mass from 5 g to some 10–500 mg, or more preferably 20–150 mg, allows for a much greater dilution effect of the sample with extraction medium, whilst still working within perfectly manageable volumes for laboratory practice. The present invention facilitates a dilution of approximately 50 volumes (v/w) compared to the extraction process of U.S. Pat. No. 5,455,160 which used a dilution of 2 volumes (v:w).

Whilst not wishing to be restricted by the theory, it may be surmised inter alia that the greater volume of extraction medium increases the accessibility of the molecular components of the sample to the medium and hence increases solubilisation of the said components, including the proteins of interest. The less concentrated the homogenate, the greater the uniformity of the liquid phase, and the less variable is the final composition in terms of pH, metal ion concentration etc, all of which can be influenced by the faeces. For such highly diluted samples the buffering, chelating or dissociating capacities of the extraction medium are not exhausted and thus the extraction yield as well as stability of the extracted material such as proteins are more easily controllable.

Provided there is sufficient dilution, the ratio between sample and extraction medium may not be critical for the extraction yield of calprotectin. This allows for a slight simplification of the procedure by mixing a weighed faecal sample with a fixed volume, e.g. 5 ml, of extraction medium. Thus, prefilled vials containing constant volumes of extraction medium may be used and the weighing of samples is the only variable step.

A further simplification of the procedure may be possible by omitting the weighing step. In the hands of an experienced laboratory technician, it is possible to collect a fairly constant amount of faecal sample, e.g. in the range of 30–50 mg. The collection of close to constant amounts of faeces may be done simply by the aid of visual inspection, or even more reproducibly by the assistance of a collecting device for such purpose, e.g. the commercial device of Boehringer (cat. No. 718211) or others. Thus, although less exact than the complete procedure comprising the weighing step, clinically satisfactory accuracy may be obtained. This is essentially due to the large differences in calprotectin levels between healthy and sick people and hence precise data is not always essential in order to be of clinical relevance.

Though extensive extraction of a carefully weighed faecal sample with a citrate-urea extraction medium has been found to give the most highly reliable quantitative results, it has also been shown that even a simplified version of the method may give surprisingly useful results.

Thus, for extractions performed with a citrate-free medium on loopfuls (about 50 mg) of faecal sample, highly significant calprotectin level differences were found between healthy and diseased persons. Without sacrificing too much accuracy, fairly reliable and reproducible results should be obtainable with this simplified version of the test, omitting the weighing step and optionally the centrifugation steps. Ultimately, it is a matter of choice, partly depending on the clinical problem, whether to select a highly accurate test, e.g. for follow-up of cancer treatments, or to choose a slightly less accurate but still clinically very useful test, even better suited for large scale screening investigations, requiring less work and thus being even more user friendly.

The nature of the buffer per se, i.e. its pH stabilising capacity, its strength and composition, may be of importance for some proteins and may contribute to the extraction and stabilising of these proteins from within the GI sample.

A preferred aspect of the invention comprises a buffered extraction medium capable of stabilising and eluting proteins from within the GI sample. In the case of calprotectin extraction, a 0.1 M Tris buffer of pH 8 gave excellent results. In the presence of citrate, the yield was even higher and the pH value of the medium proved to be of less importance; indeed, it may be possible to extract proteins using an extraction medium according to the invention within a pH range as wide as 5–10. This indicates a special role for citrate in the extraction medium which is not related to its buffering capacity, as discussed in more detail hereinafter.

Furthermore, the capacity of the extraction medium to disperse, disaggregate or de-complex the molecules could be expected to have a very great effect upon the expected protein yield. In a further preferred aspect of the invention therefore the extraction medium comprises one or more dissociating agents, preferably in approximately molar concentrations, capable of freeing protein molecules from the surrounding cells, fluids and/or faecal waste products. An example of such an agent would be SDS or urea but any other suitable agent known to one skilled in the art would suffice.

It may be noted that since dissociating agents may be detrimental to the proteins to be extracted, e.g. by causing dissociation of active molecular complexes into inactive monomers, the dissociating agent and its concentration must be selected with a view to the particular proteins of interest. It has been shown that 8M urea causes monomerisation and inactivation of calprotectin (Fagerhol et al., 1990). Therefore, the finding by the present inventors that the incorporation of 1M urea into the extraction medium was advantageous, is surprising and unexpected.

The choice of dissociating agent and its concentration should be based not only on its immediate effect upon extraction yield but also upon any effects it may have upon the stability of the proteins or other molecules of interest, particularly under storage conditions. The present inventors have shown that dissociating agents such as SDS increase the yield of calprotectin in the extract. Upon storage, however, when SDS was used in the extraction medium, the protein was susceptible to denaturation. The use of 1M urea on the other hand increased the yield in a stable manner and the addition of BSA, 0.5–2%, optionally in saline, to the extraction medium increased it further. In a preferred aspect of the invention therefore, the extraction medium further comprises one or more dissociating and/or disaggregating agents and may also further comprise bovine serum albumin (BSA).

$Ca^{2+}$ is known to bind specifically to calprotectin monomers and appears to help stabilise the calprotectin complex. Also, calcium ions are known to stabilise cell membranes in vivo by forming divalent bridges thereon. It is possible that calprotectin is linked to or constrained by material in faeces or on intestinal cells via such calcium bridges in a manner which impedes its extraction and hence decreases the calprotectin yield. If this is the case, the inclusion of calcium chelators in the extraction medium might be expected to release the calprotectin complex from insoluble cell debris and thus improve the protein yield. Also, as indicated above, the relatively pH independent effect of citrate, a known calcium chelator, suggested an effect more related to calcium binding than to its pH buffering capacity.

To study this hypothesis further, a number of calcium chelators such as EDTA, EGTA, citrate and phosphate were incorporated into the extraction medium and the effect upon calprotectin yield assessed. EDTA increased the yield of calprotectin but the protein proved to be unstable upon storage. A somewhat weaker calcium complexing agent however, in particular citrate, increased the protein yield without any significant destabilising effect. It is possible that the citrate may remove or compete with calcium binding components in the faecal sample without removing calcium from the complex itself, thus facilitating extraction without destabilising the calprotectin complex. A delicate balance between calprotectin, $Ca^{2+}$, $Ca^{2+}$ chelators and the faecal or GI samples probably has a significant influence on the extraction yield and calprotectin stability.

Consequently, in a preferred aspect of the invention, the extraction medium comprises one or more calcium chelators in concentrations of for example 10–250 mM (depending on their affinities for $Ca^{2+}$), said calcium chelator preferably being citrate but potentially any calcium chelator known to one skilled in the art.

Also, there may be other advantages to the incorporation of a chelator in the extraction medium. It is known, for example, that $Zn^{2+}$ has the ability to bind calprotectin (Raftery et al., 1996) and also that divalent metal ions ($Ca^{2+}$, $Zn^{2+}$, $Mn^{2+}$ and $Fe^{2+}$) significantly affect biological function of calprotectin (Yiu et al., 1997). Therefore, the presence of $Zn^{2+}$ may influence the extraction and/or assay of calprotectin. When the effects of $Zn^{2+}$ and several other metal ions on the assay of purified calprotectin were studied, $Zn^{2+}$ $Al^{3+}$, $Fe^{2+}$ and $Fe^{3+}$ interfered negatively with the assay, the $Fe^{2+}$ and $Fe^{3+}$ at particularly low concentrations.

This interference could be counteracted by the presence of chelators, for example citrate and/or phosphate. When GI samples were spiked with these ions the interference was less significant, probably due to the presence in faecal samples of a vast amount of bacteria, known to produce chelating substances (Finkelstein et al., 1983). Nevertheless, the observations indicated that it may be advantageous for the extraction medium to comprise chelators with a capacity for chelating ions other than calcium. Consequently, in a preferred aspect of the invention, the extraction medium comprises one or more chelating substances capable of chelating one or more other metal ions.

In the release of calprotectin from faecal samples, the enhancing effects of (calcium) chelators and dissociating agents (e.g. urea) may be antagonistic, additive or synergistic. Preliminary experiments indicate that urea and citrate are acting in an additive way, without any interdependency. Thus, whereas for two experiments on different faecal samples, urea gave about 150% yield and citrate about 225%, the combined effect was some 270%. Thus, the enhancing effect appeared to be markedly higher for citrate than for urea, but combining the two agents may be advantageous. Since relative effects may vary among samples, the combination of both these two agents, probably acting by different mechanisms, may give a better guarantee of efficient extraction from a higher number of samples.

Depending on the origin of the faecal or GI sample or the disease state or intestinal condition, the increase in calprotectin yield generated by the present invention compared to the method of U.S. Pat. No. 5,455,160 may vary considerably. For individual faecal samples, a 3 to 20 fold increase in yield was usually found using the method according to the invention compared to the prior art method, but in exceptional cases,(about 5%) no increase was observed (see Table 2, Example 4 hereinafter). The natural variation in faecal samples, including extremes such as diarrhoeic fluid and very solid material, influences the accessibility of proteins or the relevant epitopes. Thus a direct correlation between the extraction methods cannot be expected.

Protein extraction using a process as described herein produces a clear supernatant or filtrate which is suitable for subsequent protein analysis using any suitable assay known in the art, preferably immunometric methods, such as ELISA or RIA or assays which depend upon the use of membrane filters carrying antibodies to which the supernatant or filtrate may be applied directly without clogging.

Clearly, the extract may be used directly for the measurement of any proteins extracted from the sample for which a suitable assay is available, for example haemoglobin. It has been shown, for example (Gilbert et al., 1996), using assays for both hemoglobin and calprotectin, that both of these proteins, independently of each other, are indicators of GI diseases. Thus, in one extract supernatant there may be material suitable for numerous GI disease marker tests, adding to the diagnostic value of this process.

It is envisaged that large-scale screening of faecal samples from healthy persons, e.g. above 50 years of age, may be advised in the future. Present screening tests for faecal blood give a higher number of both false positive and false negative results; screening for calprotectin thus may prove useful as a supplement to such tests.

The clear and non-viscous character of the centrifuged extract obtained by the method of the present invention has the advantageous effect that the extract may be directly applied to filters in the subsequent detection or quantitation assays. Thus, for a number of faecal samples, assayed for calprotectin using a filter with specific antibodies, only about a third of them needed to be filtered after centrifugation to remove particulate matter, prior to being applied to an antibody-loaded filter. This contrasts with the prior art method where practically none of the samples were suitable for direct application to a test filter after centrifugation, and only about a tenth of the samples were suitable for such application even after filtration to remove such particlate matter.

The presently disclosed extraction process has been shown to be fast and economic, it carries a low contamination risk, is safe and operator friendly. It is inexpensive to perform and less time consuming than the prior art method. The supernatant generated is suitable for use with membrane filter technologies to which it may be applied immediately, and thus a simple and manageable complete assay may be provided.

All of the problems which beleaguered the process of the prior art have been alleviated by the present invention. By using smaller volumes one may work in a smaller scale which is compatible with the use of a closed system. The non disposable homogenising mixer rod which was used in the prior art method required thorough cleaning after each use and even then carried a risk of sample cross-contamination. In the present invention, the non-disposable rod is replaced by the single-use inoculation loop used to collect the sample, which is left in the tube during the extraction process and fulfils the function of the homogeniser rod. Such a setup allows the tube to be sealed before vortexing and results in a closed system. The use of a closed system when homogenising a faecal sample in extraction medium results in a dramatic decrease in environmental contamination with faecal bacteria relative to the method of the prior art.

Further benefits resulting from the employment of a closed system are clearly the reduction of unpleasant odours, the lower risk of cross contamination of other samples and the comparative speed and ease with which the work area may be cleaned after protein extraction from the samples.

Additionally, comparison of the time taken to conduct both the present and the prior art extraction processes reveals that the prior art process required 60 minutes to extract protein rich supernatants from 32 samples whereas the process of the present invention required only 25 to 30 minutes. Furthermore, processed samples may be stored frozen as clear supernatants. This minimises problems with homogenisation etc. after thawing.

In order to allow storage of the extraction medium and prevent microbial spoilage, preservatives, for example sodium azide, may be added to the medium as necessary.

In another aspect of the invention, a kit is provided which utilises a variation of the assay for calprotectin provided by Fagerhol et al. in US 5,455,160 wherein an antibody based method of detection is coupled with a membrane filter/card system and used to provide a qualitative and/or quantitative determination of the calprotectin in the GI tract sample extract.

In a preferred embodiment of the invention a NYCO-CARD™ is used. Thus a nitrocellulose membrane or a nylon membrane, for example HYBOND N® (sold by Amersham International) or MAGNA NYLON® (sold by MSI) is used as the filter. A pore size of 0.22 or 0.45 $\mu$m is convenient. The membrane carries antibodies capable of binding to the target molecule, for example calprotectin. An absorbent pad such as cellulose blotting paper is placed on one side of the membrane to enhance passage of the liquid sample through the membrane. A liquid impermeable sheet or frame is placed over the other side of the membrane. Circular holes e.g. of 5 mm diameter, are provided in the impermeable sheet or frame to allow accurate application of the liquid sample and assay liquids to the membrane. A known volume of the sample e.g. 10–500 $\mu$l is applied to the membrane and allowed to pass into the absorbent pad underneath. An aqueous solution e.g. 10–500 $\mu$l of antibody conjugated to gold-sol colloid as marker is applied and allowed to pass through the membrane. The membrane is then washed with 2×200 $\mu$l aliquots of a suitable washing liquid, for example Tris HCl buffer (pH 7.0), before the quantity of gold sol immobilised on the membrane is assessed usually by the naked eye by comparison to a colour scale or by a reflectometer. The extraction liquid according to the invention can also be used for the further simplification of faecal calprotectin assays using simple dipstick or membrane-based formats. Clinical studies show that the method of the invention is as clinically relevant and reliable as the method of Roseth et al. (1992) and provide strong evidence of a close correlation between faecal calprotectin levels and the degree of colorectal neoplastic disease.

The present invention will now be illustrated further by the following non-limiting Examples.

EXAMPLE 1a

An example of the extraction medium (aqueous stock solution) was prepared as follows:

| | |
|---|---|
| 0.25 M | Tris |
| 0.25 M | citric acid |
| 2.5 M | urea |
| 0.025 M | $CaCl_2$ |
| 1.25% | bovine serum albumin (BSA) |
| 0.05% | sodium azide |

The pH is adjusted to pH 8.0 using NaOH and the medium filtered using 0.22 $\mu$m pore diameter filters. The medium may then be stored at room temperature for approximately 3 months or at 4° C. for approximately 12 months.

EXAMPLE 1b

A simplified version of the extraction medium prepared in Example 1a may be prepared as follows:

| | |
|---|---|
| Tris | no change |
| citric acid | omitted |
| urea | no change |
| $CaCl_2$ | no change |
| BSA | 1% instead of 0.5% (final) |
| azide | replaced by merthiolate; saline added |

EXAMPLE 2a

A process for the extraction of the protein calprotectin from a sample of human faeces. The following experimental procedure was followed:

1. 50–100 mg faecal sample was collected and weighed with a disposable inoculating loop.
2. The loop and the sample were transferred into a 14 ml extraction tube.
3. A stock solution of the extraction medium was prepared as in Example 1a above. The stock solution was diluted 2.5 times with water and added to the tube to provide a total dilution factor of 1:50.
4. The tube was sealed and the faecal sample was homogenised in the extraction medium.
5. Homogenisation took place by vortexing for approximately 30 seconds and then shaking for 20 minutes at 1400–1800 rpm on a shaker with the disposable inoculating loop still remaining in the tube.
6. 1 ml of the crude extract was centrifuged in an Eppendorf 2TM mini-centrifuge tube at 10,000 g for 20 minutes to obtain a clear supernatant. The supernatant thus produced is suitable for use in any assay to determine specific protein concentration.
7. The supernatant thus acquired may be stored at −20° C.

EXAMPLE 2b

A simplified version of the process described in Example 2a may be performed without the weighing and centrifugation steps and using the extraction medium described in Example 1b as follows:

1. Part of the faecal sample is homogenized with a rod before collecting material for tests.
2. Two loopfuls (disposable inoculating loop, each loopful about 100 mg) of homogenized faecal material is put into 10 ml extraction medium (as described in Example 1b) in a screwcapped tube. The loop is rinsed with the extraction medium.
3. The sealed tube is vortexed for 20–30 seconds.
4. The tube is placed on a sample rotator (1–2 rpm) for at least 20 minutes.
5. Debris is allowed to settle for 5–10 minutes.
6. From the top 50 µl is collected for assaying.

Alternatively, a portion of 100 µl may be frozen at −18° C. until tested.

EXAMPLE 3
Monitoring of Risk of Environmental Contamination

The spread of bacteria during the preparation of the extract was assessed by placing nutrient agar plates, suitable for the culture of coliforms and other gram negative bacteria, in the immediate vicinity of the work station (approximately 10 to 20 cm) during both the prior art process and the extraction process of the present invention. The plates were collected after preparation of the extract, incubated overnight at 37° C. and the number of colonies counted the next day. The methods and the bacterial count generated are illustrated below and also in FIG. 1.

|  | colonies noted on test plates |
| --- | --- |
| Prior art method |  |
| homogenising | 50–100 colonies |
| rinsing | above 200 colonies |
| Method of the invention |  |
| all steps | 5 colonies |

Comparison of the number of colonies generated by the two different methods shows that very little faecal contamination of the surrounding area occurs with the present invention compared with that of the prior art.

EXAMPLE 4
Extraction Yield of Calprotectin by New and Prior Art Methods (a) Establishing the Total Amount of Calprotectin.

To obtain an estimate of the total amount of calprotectin in faecal samples, four such samples, representing low and high values of calprotectin, were extracted five times using the procedure of Example 2, and in each extract the amount of calprotectin was determined by ELISA. For all the samples, the fifth extract contained only small amounts of calprotectin and thus the sum of calprotectin detected in the five extracts was taken as being representative of the total amount present in each sample.

(b) Yield from a Single Extraction Using the New and Prior Art Methods

The method of Example 2a was used to extract calprotectin once from four faecal samples using the new and the prior art method. Table 1 shows the yield obtained.

TABLE 1

Extraction yield with the 5 g prior art method compared to the 50 mg method of the present invention from four representative samples.

| | New Method | | Total | Prior art method | |
| --- | --- | --- | --- | --- | --- |
| Sample No. | Result (mg/l) 50 mg | % Yield 50 mg | Calprotectin in sample * (mg/l) | Result (mg/l) 5 g | % Yield 5 g |
| 11 | 417 | 52 | 802 | 116 | 14 |
| 19 | 1005 | 65 | 1546 | 85 | 5 |
| 30 | 26 | 76 | 34 | 6 | 18 |
| 31 | 177 | 80 | 221 | 33 | 15 |

* Total calprotectin in each sample was estimated as the sum of calprotectin yield from five extractions with the 50 mg method of the present invention.

For the four samples the yield varied between 52 and 80% (new method), as compared to 5–18% with the prior art method.

(c) Ratio of Calprotectin Values Found by the New and the Prior Art Method

Faecal samples were extracted once for calprotectin by the method of Example 2a and the prior art method. calprotectin levels were determined by ELISA and ratios for the two methods are presented in Table 2.

TABLE 2

Ratio between calprotectin yield with the prior art (5 g) and new (50 mg) extraction method.

| | Total Calprotectin (mgl/l) | | Ratio |
| --- | --- | --- | --- |
| Sample No. | New method 50 mg | Prior art 5 g | (new/prior art) 50 mg/5 g |
| 1 | 18 | 9 | 2.0 |
| 2 | 116 | 46 | 2.5 |
| 3 | 26 | 14 | 1.9 |
| 4 | 110 | 52 | 2.1 |
| 5 | 712 | 117 | 6.1 |
| 6 | 17 | 12 | 1.4 |
| 7 | 844 | 43 | 19.6 |
| 8 | 116 | 43 | 2.7 |
| 9 | 475 | 116 | 4.1 |
| 10 | 96 | 20 | 4.8 |
| 11 | 43 | 26 | 1.7 |
| 12 | 18917 | 20000 | 0.9 |
| 13 | 36 | 9 | 4.0 |
| 14 | 1233 | 85 | 14.5 |
| 15 | 450 | 100 | 4.5 |
| 16 | 1984 | 115 | 17.3 |
| 17 | 39 | 7 | 5.6 |
| 18 | 194 | 175 | 1.1 |
| 19 | 93 | 33 | 2.8 |
| 20 | 1754 | 250 | 7.0 |
| 21 | 119 | 38 | 3.1 |
| 22 | 83 | 38 | 2.2 |
| 23 | 53 | 9 | 5.9 |
| 24 | 140 | 36 | 3.9 |
| 25 | 27 | 6 | 4.5 |
| 26 | 201 | 33 | 6.1 |
| 27 | 42 | 11 | 3.8 |
| 28 | 176 | 29 | 6.1 |

Median ratio: 3.9
Range ratio: 0.9–19.6

The ratios obtained for the two methods varied from 0.9 to 19.6, with a median of 3.9. The lack of correlation between the two methods is most likely due to the small and highly variable extraction yield of the prior art method (Table 1). However, with the exception of two samples (2 and 18), yields were 40–2000% greater in the new method.

EXAMPLE 5
Determination of Calprotectin by ELISA and Calprotectin and Haemoglogin using a Filter Technique (NYCOCARD™)

From 16 faecal samples from colorectal-cancer patients, calprotectin and haemoglobin were extracted by the procedure of Example 2. The clear supernatants were used for determination of calprotectin by an ordinary ELISA method and for the determination of calprotectin and haemoglogin using a filter card (NYCOCARD™) using a gold-labelled monoclonal antibody conjugate. Measured values are given in Table 3.

TABLE 3

Calprotectin and hemoglobin measurements* in 16 faecal samples from patients with colorectal cancer.

| Sample No. | Calprotectin (mg/l) ELISA assay | Calprotectin (mg/l) NycoCard filter assay | Haemoglobin (mg/l) NycoCard filter assay |
|---|---|---|---|
| 1 | 777 | 691 | 344 |
| 2 | 126 | 138 | 0 |
| 3 | 123 | 170 | 6 |
| 4 | 196 | 310 | 0 |
| 5 | 166 | 260 | 0 |
| 6 | 339 | 494 | 31 |
| 7 | 83 | 96 | 0 |
| 8 | 129 | 221 | 0 |
| 9 | 202 | 337 | 73 |
| 10 | 144 | 227 | 181 |
| 11 | 173 | 166 | 12 |
| 12 | 190 | 233 | 19 |
| 13 | 1146 | 1276 | 5 |
| 14 | 1010 | 1130 | 91 |
| 15 | 406 | 576 | 64 |
| 16 | 2062 | 2144 | 191 |

*Supernatants were extracted using method of the invention.

There would appear to be no correlation between the amount of calprotectin and haemoglobin measured in the assayed faecal samples. This may be explained by their apparently independent nature as markers for cancer (Gilbert, et al., 1996).

Bibliography

Fagerhol, M. K., Andersson KB, Naess-Andresen CF, Brandtzaeg P, Dale I. (1990) CaAprotectin The L1 Leukocyte Protein. In: Smith V L and Dedman J R (eds.) *Stimulus response coupling: the role of intercellular calcium-binding proteins*. CRS Press Inc. pp. 187–210.

Finkelstein, R. A., C. V. Sciortino, and M. A. McIntosh. (1983) Role of Iron in Microbe-Host Interactions. *Revs. Infect. Dis.* 5: Suppl. 4. S759–S777.

Gilbert J. A., Ahlquist D. A., Mahoney D. W., Zinsmeister A. R., Rubin J. & Ellefson R. D.(1996) Fecal marker variability in colorectal cancer: Caiprotectin versus hemoglobin *Scand. J. Gastroenterol*. 31:

Raftery, M. J., Harrison, C. A., Alewood, P., Jones, A. & Geczy, C. L. (1996) Isolation of the murine S100 protein MRP14 (14 kDa migration-inhibitory-factor-related protein) from activated spleen cells: Characterization of post-translational modifications and zinc binding. *Biochemnical Journal* 316: Part, 1, 285–293.

Røseth, A. G., Fagerhol, M. K., Aadland, E. and Schonsby, H. (1992) Assessment of the neutrophil dominating protein caiprotectin in faeces. A methodologic study. *Scand. J. pastroenterol*. 27s 793–798.

Røseth A G, Kristinsson J, Fagerhol M K et al., (1993) Faecal calprotectin: A novel test for the diagnosis of colorectal cancer? *Scand. J. Gastroenterol*. 28:(12): 1073–1076.

Young G P and St. John D J B, (1992) Faecal occult blood tests: choice, usage and clinical applications. *Clin. Biochem Revs* . 13: 161–167.

Yui S., Mikami, M., Tsurumaki M. and Yamazaki M. (1997) Growth-inhibitory and apoptosis-inducing activities of calprotectin derived from inflammatory exudate cells on normal fibroblasts: Regulation by metal ions. *J. Leuk. Biol*. 61: 50–57.

U.S. Pat. No. 4,833,074

U.S. Pat. No. 5,455,160

What is claimed is:

1. A process for extracting calprotectin from faeces or gastrointestinal (GI) tract content samples taken from humans or other mammals, comprising;
   (a) mixing 10–500 mg of sample with an amount of aqueous extraction medium effective to extract said calprotectin and comprising urea and optionally further comprising one or more dissociating, disaggregating and/or chelating agents;
   (b) homogenising the sample in a closed vessel;
   (c) separating the solid and liquid materials of the dispersion, and
   (d) recovering the clear liquid extract.

2. A process as claimed in claim 1 wherein said GI sample is obtained by gastroscopy, endoscopy or by using any other invasive or non-invasive technique known in the art.

3. A process as claimed in claim 1 wherein said GI sample is faeces.

4. A process as claimed in claim 1 wherein the amount of said sample is between 20 and 150 mg.

5. A process as claimed in claim 1 wherein the aqueous extraction medium of step a) is in approximately 50 fold excess v/w ratio relative to the weight of sample used.

6. A process as claimed in claim 1 wherein said sample is collected using a disposable inoculating loop and said inoculating loop remains enclosed in the vessel during the homogenising step (b).

7. A process as claimed in claim 1 wherein the solid and liquid materials are separated in step c) by centrifugation and/or by filtration.

8. A process as claimed in claim 1 wherein the sample is mixed with a pre-determined fixed . volume of excess aqueous extraction medium.

9. A process as claimed in claim 1 wherein the sample is weighed prior to mixing with the aqueous extraction medium.

10. A process as claimed in claim 1 wherein the pH of the extraction medium is between 5 and 10.

11. A process as claimed in claim 1 wherein the extraction medium is buffered to approximately pH 8.

12. A process as claimed in claim 11 wherein said buffer comprises approximately 0.1M Tris.

13. A process as claimed in claim 1 wherein the extraction medium further comprises one or more metal ion chelators.

14. A process as claimed in claim 13 wherein said chelator is selected from the group consisting of citrate, EDTA, EGTA and phosphate.

15. A process as claimed in claim 14 wherein said extraction medium comprises citrate between 10 and 250 mM.

16. A process as claimed in claim 1 wherein the extraction medium further comprises a dissociating agent.

17. A process as claimed in claim 16 wherein said dissociating agent is SDS (sodium dodecyl sulfate).

18. A process as claimed in claim 1 wherein urea is incorporated into the extraction medium in approximately 1 molar concentration.

19. A process as claimed in claim 1 wherein said extraction medium further comprises BSA (bovine serum albumin).

20. A process as claimed in claim 19 wherein said BSA is incorporated into the extraction medium at a concentration of approximately 0.5–2%.

21. A process as claimed in claim 1 wherein the concentration of a protein contained within the extract is measured.

22. A process as claimed in claim 21 wherein said protein is calprotectin and/or haemoglobin.

23. A process as claimed in claim 1 wherein the protein concentration is measured by immunoassay.

24. A process as claimed in claim 23 wherein said immunoassay is selected from the group consisting of ELISA, RIA and membrane filter based assays.

25. A process as claimed in claim 1 wherein the extraction medium further comprises one or more anti-spoilage agents.

* * * * *